US007005097B2

(12) United States Patent
Wang et al.

(10) Patent No.: US 7,005,097 B2
(45) Date of Patent: *Feb. 28, 2006

(54) MEDICAL DEVICES EMPLOYING CHAIN EXTENDED POLYMERS

(75) Inventors: Lixiao Wang, Long Lake, MN (US); Jeffrey S. Lindquist, Maple Grove, MN (US); Nao Lee, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 145 days.

This patent is subject to a terminal disclaimer.

(21) Appl. No.: 10/055,747

(22) Filed: Jan. 23, 2002

(65) Prior Publication Data

US 2003/0152728 A1   Aug. 14, 2003

(51) Int. Cl.
*B32B 1/08* (2006.01)
(52) U.S. Cl. .................. 264/241; 264/418; 428/36.9
(58) Field of Classification Search ............ 428/35.7, 428/36.9; 264/211.21, 211.23, 328.19, 331.13, 264/331.15, 331.19, 241, 418
See application file for complete search history.

(56) References Cited

U.S. PATENT DOCUMENTS

| 4,490,421 | A |   | 12/1984 | Levy .................... 428/35 |
| 4,857,603 | A | * | 8/1989 | Akkapeddi et al. ....... 525/437 |
| 4,950,239 | A |   | 8/1990 | Gahara et al. ............ 604/96 |
| 4,963,313 | A |   | 10/1990 | Noddin et al. ........... 264/573 |
| 5,108,412 | A |   | 4/1992 | Krumeich et al. |
| 5,264,260 | A |   | 11/1993 | Saab ..................... 428/35.5 |
| 5,348,538 | A |   | 9/1994 | Wang et al. .............. 604/96 |
| 5,500,180 | A |   | 3/1996 | Anderson et al. .......... 264/532 |
| 5,554,120 | A |   | 9/1996 | Chen et al. .............. 604/96 |
| 5,556,383 | A |   | 9/1996 | Wang et al. .............. 604/96 |
| 5,714,110 | A |   | 2/1998 | Wang et al. ............. 264/529 |
| 5,797,877 | A |   | 8/1998 | Hamilton et al. .......... 604/96 |
| 5,807,520 | A |   | 9/1998 | Wang et al. ............. 264/520 |
| 5,922,443 | A |   | 7/1999 | Larsen et al. ............ 428/217 |
| 6,228,980 | B1 |   | 5/2001 | Loontjens et al. ......... 528/480 |
| 6,265,016 | B1 |   | 7/2001 | Hostettler et al. ........ 427/2.11 |
| 6,426,145 | B1 | * | 7/2002 | Moroni ................... 428/412 |
| 6,504,004 | B1 | * | 1/2003 | Zahr ..................... 528/310 |
| 2001/0001113 | A1 |   | 5/2001 | Lim et al. .............. 604/96.01 |

FOREIGN PATENT DOCUMENTS

| EP | 0 288 253 |     | 10/1988 |
| EP | 0799623 A2 | * | 10/1997 |
| EP | 0 799 623 |     | 9/1999 |
| WO | WO 96/34909 |   | 11/1996 |
| WO | WO 99/03863 |   | 1/1999 |
| WO | WO 99/44649 |   | 9/1999 |

OTHER PUBLICATIONS

International Search Report dated Jul. 7, 2003 for PCT/US03/02595, submitted by applicants on Jul. 17, 2003.*
B. Scholtens. et al "A New Chain Extender System for High Molecular Weight (HMW) Polyamides and Polyesters," DSM Presentation Slides (Apr. 24, 2001).

* cited by examiner

*Primary Examiner*—Sandra Nolan Rayford
(74) *Attorney, Agent, or Firm*—Vidas, Arrett & Steinkraus

(57) ABSTRACT

Medical devices such as catheters and balloons are formed from a thermoplastic polymer composition comprising a melt mixture product of at least one terminally reactive polymer and a chain extender.

19 Claims, No Drawings

MEDICAL DEVICES EMPLOYING CHAIN EXTENDED POLYMERS

FIELD OF THE INVENTION

The present invention relates to the field of medical devices made from thermoplastic polymers, especially devices inserted into the body, for instance tubular devices such as catheters and high strength balloons used thereon, and to polymer compositions used to prepare such devices.

BACKGROUND OF THE INVENTION

A wide variety of medical devices are made from thermoplastic polymers. Medical devices must be manufactured with greater care than general consumer products especially when inserted into the body or brought into contact with a wound or lesion. In the area of treatment devices, such as catheters, manufacturers must take great care to assure that the devices perform with an extremely high degree of reliability. At the same time there is a need to develop materials and improve processing techniques to obtain improvements in desirable properties such as tensile strength, flexibility, puncture resistance, and softness. One area in which development has been especially intense focuses on balloons deployed on catheters which are utilized for dilatation, especially angioplasty, for stent placement, for urinary treatment, and the like.

In preparing high strength balloons for medical devices such as dilatation and stent placement catheters, a variety of polymer materials have been used.

Levy, U.S. Pat. No. 4,490,421, describes use of PET of high molecular weight (1.0 IV or higher). The patent notes that the IV may decrease during processing into balloons. Such a decrease is believed to be related to polymer degradation caused by extrusion temperature and the time the resin is held in the melt. Lower molecular weight PET has also proven useful for preparing high strength balloons. See for instance Noddin et al, U.S. Pat. No. 4,963,313; Saab, U.S. Pat. No. 5,264,260; Wang et al U.S. Pat. No. 5,348,538.

Polyamide balloons are described in Pinchuk, U.S. Pat. No. 5,108,412. Polyurethane block copolymer balloons are described in Gahara, U.S. Pat. No. 4,950,239, and Anderson et al, U.S. Pat. No. 5,500,180. Polyamide block copolymer balloons and polyester block copolymer balloons are described in Wang et al, U.S. Pat. No. 5,563,383. Various other polymers have also been used for catheter balloons.

A wide variety of polymer blends have also been described for such balloons, for instance, Sahatjian et al, U.S. Pat. No. 5,500,180; Chen et al, U.S. Pat. No. 5,554,120, Hamilton et al, U.S. Pat. No. 5,797,877. Some such blends have included compatibility enhancing additives. However, heretofore it has not been proposed to include additives which maintain or increase molecular weight during melt processing.

A typical process for forming catheter balloons involves extruding a tube of thermoplastic polymer material from a melt composition and then blowing the extruded tube at an elevated temperature above the $T_g$ (using highest $T_g$ in case of block copolymers), optionally with ambient or elevated temperature stretching, to form the balloon with a radial and/or longitudinal molecular orientation. See e.g. Wang et al U.S. Pat. No. 5,348,538, Wang et al, U.S. Pat. No. 5,563,383; and Wang et al, U.S. Pat. No. 5,714,110. The ability of the extruded tubing material to successfully be processed in this manner is thus an important requirement of polymer compositions used to form catheter balloons.

For instance, in practice, the polyester PBT (polybutylene terephthalate), and some butylene terephthalate copolymers, were observed to produce extruded tubing which had a tendency to opacify and/or to resist thermal forming into a balloon configuration. In WO99/44649 boric acid is added to PBT and butylene terephthalate copolymers to improve post-extrusion processing characteristics of such polymers when forming catheter balloons.

In some thermoplastic polymer processing arts it has been proposed to maintain or increase the molecular weight of polyesters or polyamides by adding to a polymer melt a difunctional additive which can react with polymer chain ends to extend chains. Chain extending melt additives have been described for polyesters and polyamides which have a relative low tendency for crosslinking. Examples of such additives are described in U.S. Pat. No. 6,228,980, WO 96/34909, and EP 0288253. However, before the present invention, the suitability of such additives in the manufacture of medical devices has not been explored. Nor does it appear that the effects of such additives on post-extrusion sub-melt thermal formability of polymer compositions have been considered.

SUMMARY OF THE INVENTION

One aspect of the invention pertains to medical devices made from thermoplastic polymers, especially devices inserted into the body, for instance tubular devices such as catheters and high strength balloons used thereon, which are formed from melt compositions of the polymer and a chain extending additive. The chain extending additive is desirably employed in an amount which increases molecular weight but which does not substantially promote or induce crosslinking.

Other aspects of the invention are catheter or balloon forming processes in which chain extending additives are incorporated in an extrusion melt used to produce a tube. The tube is then processed to form a catheter or a balloon.

The polymers can have thiol, hydroxyl, amine and/or carboxylic acid terminal groups. They may be for instance polyesters, polyamides, polyurethanes, block copolymers incorporating a polyester, polyamide, polyurethane and/or polyether segment or blends comprising such polymers. In some embodiments the chain extending additive may comprise a bis-caprolactam compound, a bis-oxazoline and/or bis-oxazine compound.

The inventive balloons in some embodiments may provide improvements in properties such as burst strength, fatigue resistance, flexibility, durability, impact resistance, puncture resistance and/or kink-resistance.

DETAILED DESCRIPTION OF THE INVENTION

All published documents, including all U.S. patent documents, mentioned anywhere in this application are hereby expressly incorporated herein by reference in their entirety. Any copending patent applications, mentioned anywhere in this application are also hereby expressly incorporated herein by reference in their entirety.

The polymer compositions of the invention include at least one "terminally reactive" polymer, which for purposes of this application, is a polymer which has at least one terminal group on at least some of the molecules thereof which can be reacted with the chain extending additive compound in a way which forms a covalent bond between the polymer chain and a residue of the chain extending compound. When the chain extender reacts with terminal groups of two different polymer molecules the polymer average chain length and molecular weight is increased. Exemplary terminal groups of the terminally reactive polymer may be carboxylic acid groups and active hydrogen groups such as hydroxyl, amine and, to a lesser extent, thiol groups. Preferably the terminally reactive polymer will have few, or substantially no, groups along the polymer chain which have similar or greater reactivity with the selected chain extender compound(s). The terminally reactive polymers may be polyesters, polyamides, polyurethanes, block copolymers incorporating a polyester, polyamide, polyurethane and/or polyether segment or blends comprising such polymers. The terminally reactive polyester or polyamide polymers may be homopolymers, random copolymers or alternating copolymers. Blends of more than one terminally reactive polymer may also be employed. Specific examples of terminally reactive polymers include polyethylene terephthalate (PET), polybutylene terephthalate (PBT), polyethylene terephthalate/isophthalate copolymers, nylon 6,6, nylon 11, nylon 12, polyamide/polyether/polyester block copolymers such as PEBAX® resins, in particular PEBAX 6333, 7033 and 7233, polyester/polyether block copolymers such as ARNITEL EM 740 from DSM Engineering Plastics and polyurethanes such as ISOPLAST 301 and PELLETHANE 2363-75D from Dow Chemical Company.

Blends comprising a terminally reactive polymer and another thermoplastic polymer which is not a terminally reactive polymer may also be used. Examples include polyolefins, poly(meth)acrylate esters, silicones, and various organic rubbers. Suitably, the blend polymer(s) have substantially no hydroxyl, amine, thiol and/or carboxylic acid groups along the polymer chain. Particular examples are olefin modified polyesters such as SELAR PT resins of the 4000 series, and blends thereof with 50–99% PET.

A variety of chain extending additives which will react with some or all of the reactive polymer terminal groups are known which can be effectively employed in the invention in amounts which increase molecular weight but are essentially non-crosslinking. The chain extending additive may comprise a bis-lactam compound such as carbonyl biscaprolactam (CBC) available from DSM under the ALLINCO trademark. Other suitable chain extending additives may be bis-oxazoline and bis-oxazine compounds, for instance 1,4-phenylene bisoxazoline (1,4-PBO) also available from DSM under the ALLINCO trademark, and 2,2'-m-phenylene bis (2-oxazoline) (1,3-PBO) which may be obtained from Takeda Chemical, Osaka, Japan or from Mikuni Pharmaceutical Industrial Co., LTD, Japan. An extender product described as a modified polyamide 6 is available for polyamide chain extension is sold under the trademark BRUG-GOLEN® M 1251 by Brüggemann Chemical.

The bis-lactam compound may be represented by the following general formula (I):

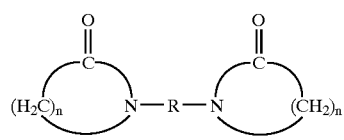
(I)

in which one or more of the methylene hydrogen atoms may alternatively be substituted by an alkyl or aryl radical; R represents a divalent organic radical; and n is an integer of 2–15.

In one embodiment R may be

(II)

where A is a divalent organic group. Suitably A is a hydrocarbon group of about 20 carbons or less or a (poly)ether group. Examples of suitable groups A include alkylene groups, such as methylene, ethylene, 1,2 propylene, 1,3 propylene, and hexamethylene; arylene groups, such as phenylene, methylphenylene, naphthylene, 4,4'-biphenylene, a bisphenol A residue and a bisphenol S residue; alkarylene groups such as ethylenephenylene, and the like; and ether interrupted hydrocarbon groups, such as ethyleneoxyethylene, (polyethyleneoxy)ethylene, (polyethyleneoxy)propylene, (polypropyleneoxy)ethylene and the like.

In another embodiment R may be

(III)

where B is —NH-A-NH, and A is as previously defined.

In still further embodiments the group R may simply be a carbonyl group, i.e.

(IV)

Compounds employing such carbonyl linkages are designated as "carboxyl bis-lactams." Suitable carbonyl bislactam compounds may have the formula:

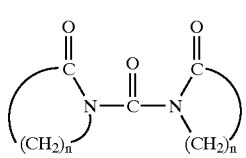
(V)

in which n is an integer of between 3 and 15. Preferably n=5 to 12.

Bis-lactam compounds useful in the invention are described in the incorporated documents U.S. Pat. No. 6,228,980 WO 96/34909 and EP 0288253. Specific examples include N,N'-isophthaloyl bis-caprolactam, N,N'-adipoyl bis-caprolactam, N,N'-terephthaloyl bis-laurolactam, N,N'-isophthaloyl bis-butyrolactam, and carbonyl bis-caprolactam.

The amount of bis-lactam compound used in the process according to the invention may vary within a wide range. Usually, a suitable amount will be within the range of from about 0.05 wt. % to about 5%, relative to the terminally reactive polymer, preferably about 0.1 to 0.7%. Typically the amount of bislactam will be adjusted to a small stoichiometric excess based on a 2:1 ratio of hydroxyl and/or amine groups on the terminally reactive polymer per molecule of bis-lactam. Alternatively, the increase in melt viscosity to be realized as a result of the desired molecular weight increase may be determined and the amount of bis-lactam adjusted accordingly.

Another group of suitable chain extenders useful in the invention are bis-oxazolines and bis-oxazines. Use of the bis-oxazoline or bis-oxazine component, alone or in combination with a bis-lactam, may be indicated when there is a substantial proportion of carboxyl terminally reactive groups. The bis-oxazoline or bis-oxazine are both described by the formula (VI):

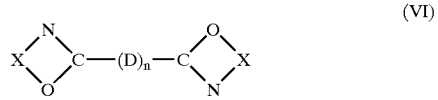
(VI)

where X is a divalent hydrocarbon group and the ring is a 5-membered ring for the bis-oxazoline or a 6-membered ring for the bis-oxazine, respectively; n=0 or 1; and D is a divalent organic group. X may be an ethylene group, a substituted ethylene group, a trimethylene or a substituted trimethylene group. As substituent, for instance an alkyl group with 1 to 10 carbon atoms, an aryl group, a cycloalkyl group or an aralkyl group may be present. Examples of an alkyl group are methyl, ethyl, hexyl, alkylhexyl, nonyl, etc.; of an aryl group are phenyl, naphthyl, diphenyl, etc.; and an example of a cycloalkyl group is cyclohexyl. D is suitably a hydrocarbon group, for instance an alkylene group, an arylene group, a cycloalkylene group and an aralkylene group.

Examples of bis-oxazolines and bis-oxazines are 2,2'-bis (2-oxazoline), 2,2-bis(4-methyl-2-oxazoline), 2,2'-bis(4-phenyl-2-oxazoline), 2,2'-bis(4-hexyloxazoline), 2,2'-p or m-phenylene bis(2-oxazoline), 2,2'-tetramethylene bis(4,4'-dimethyl-2-oxazoline) and the corresponding oxazines. Preference is given to 2,2'-bis(2-oxazoline), 2,2'-p- phenylene bis(2-oxazoline) (1,4-PBO), 2,2'-m-phenylene bis(2-oxazoline) (1,3-PBO) and the corresponding oxazines.

The quantity of bis-oxazoline or bis-oxazine used in the polymer compositions employed in the invention may vary widely depending on the reactive polymer chosen, the desired increase in molecular weight or melt viscosity, and the selected bis-oxazoline or bis-oxazine. Typically the amount of bis-oxazoline or bis-oxazine will be adjusted to a small stoichiometric excess based on a 2:1 ratio of terminal carboxyl groups per bis-oxazoline or bis-oxazine molecule. Usually a suitable amount will be within the range of from about 0.05 wt. % to about 4%, preferably between 0.1 and 2.5%, relative to the terminally reactive polymer.

When the chain extender is a modified polyamide which is reactive as a chain extender, such as BRUGGOLEN® M 1251, a suitable amount will typically be within the range of from about 0.05% to about 5% by weight, preferably between 0.2 and 4%, relative to the terminally reactive polymer.

Depending on the temperature and the particular polymer structure, thermoplastic polymers in melt form have a limited time before they display evidence of degradation in appearance or other physical properties. Desirably the chain extender compound is a compound which, at a temperature above the polymer melt temperature, has a reaction rate with the polymer terminal groups which is sufficient to react a substantial portion of the terminally reactive groups of the polymer in a time which is substantially less than the time at said temperature at which the polymer begins to display degradation. In this way the desired properties of the polymer may be maintained or improved in the melt state.

While the amounts of chain extender employed in the polymer compositions given above are believed to be generally suitable, it will be understood that the ranges of chain extender employed in individual compositions at specific melt/extrusion conditions may be further adjusted according to observed phenomena such as excessive extrusion whitening (opacity) or gel particle formation.

The process of incorporating the chain extender compound(s) can be carried out in a simple manner using the usual extruder melt-mixing techniques and equipment, for example by dry blending the terminally reactive polymer and the chain extender in a solid state. In some cases a sirvall quantity (preferably no more than about 0.2%) of an oily processing aid may be added to the dry mix to improve the uniformity of distribution of the chain extender in the dry mix. The dry mix so obtained, is then melted in a conventional melt-mixing apparatus, for example a single- or double-screw extruder. Alternatively the polymer composition may be prepared in another type of melt mixer and ten subsequently provided to the extruder directly from the initial melt mixer. The different components can also be fed to the extruder or other mixing apparatus separately. Chain extenders, in any form, can be fed into an extruder separately from the polymer resin by continuous feeding equipment available, for instance, from Doier Waegetechnik-Engelhardt GMBH, Germany which can dose feed powder from 100 gram to 5 kg in one hour. The melted blend is suitably brought to a temperature and kept for a time sufficient to react the desired proportion of the relevant terminally reactive groups of the polymer, hence being controllable.

Suitably the terminally reactive polymer and any other polymers incorporated into the polymer composition are thoroughly dried before melt blending with the chain extender component.

The polymer compositions may also contain other additives which may be useful in medical device balloons such as antioxidants, lubricants, crystallization accelerators or inhibitors, and/or drugs.

The polymer compositions of the invention may then be processed into medical devices, such as catheters or balloons in any conventional manner. In the particular case of balloons this may be by extruding a tube of the polymer composition and then blow molding, or free-blowing, the extruded tube at an elevated temperature above the $T_g$ (using highest $T_g$ in case of block copolymers), optionally with ambient or elevated temperature stretching, to form the balloon with a desired radial and/or longitudinal molecular orientation.

The extruded tube may be formed of a single layer of polymer composition or it may be a multilayer laminate. In the case of a multilayer (2 or more layers) tube, a polymer composition of the invention may be employed in some, or all, of the layers and the layers may employ the same or different polymers or polymer blends.

The invention is illustrated by the following non-limiting examples.

EXAMPLES

Example 1

Five grams (0.1%) of Mineral oil from ExxonMobile was added into 5000 grams PEBAX 7233 from AtoFina. The two chemicals were mixed by hand in a plastic bag until mineral oil was coated uniformly. Then 0–50 grams (0–1%) of Allinco CBC (carbonyl bis(1-caprolactam)) from DSM was added to the PEBAX resin. The components were dry mixed until CBC powders were evenly distributed in the resin. The composition was desiccant dried at 190° F. for 8–12 hours until a desired dryness was achieved and then extruded into tubes at a temperature in the range of 345–465° F. The extruder had multiple heat settings in each of the feeding, barrel, and setup zones. The extruder zone temperatures used were: feeding zone, 345° F.; barrel zones 365 and 395° F.; and die zones set to the extrusion temperature indicated in Table 1. The tubes were stretched and blow-molded from the stretched tubes. The balloons were formed and tested by methods disclosed in U.S. Pat. Nos. 5,556,383 and 5,807,520. The strength, burst pressure, compliance, double wall thickness were measured. The specific chain extender concentrations, extrusion temperatures, tubing dimensions, molded balloon diameters and balloon performance data are given below in Tables 1–3 where all data are averages for at least two balloons.

TABLE 1

Burst and Distension Tests of Pebax 7233 and CBC Chain Extender Compositions

| CBC Conc. (% wt) | 0 | 0.25 | 0.5 |
|---|---|---|---|
| Extrusion Temperature °F. | 395 | 465 | 465 |
| ID × OD (inch) | .0215 × .0395 | .0215 × .0395 | .0215 × .0395 |
| Balloon size (mm) | 3.0 | 3.0 | 3.0 |
| Double Wall Thickness (inch) | .00175 | .00165 | .00190 |
| Burst Pressure (psi) | 353 | 382 | 397 |
| Distension 6–12 atm (%) | 6.0 | 5.2 | 5.4 |
| Distension 12–18 atm (%) | 5.7 | 4.1 | 3.3 |
| Wall Strength (psi) | 26700 | 29805 | 26077 |

TABLE 2

Burst and Distension Tests of Pebax 7233 and CBC Chain Extender Compositions

| CBC Conc. (% wt) | 0.25 | 0.4 | 0.6 | 0.8 |
|---|---|---|---|---|
| Extrusion Temperature ° F. | 446 | 446 | 446 | 446 |
| ID × OD (inch) | .0176 × .0342 | .0176 × .0342 | .0176 × .0342 | .0176 × .0342 |
| Balloon size (mm) | 3.0 | 3.0 | 3.0 | 3.0 |
| Double Wall Thickness (inch) | .00143 | .00150 | .00155 | .00150 |
| Burst Pressure (psi) | 362 | 382 | 397 | 382 |
| Distension 6–12 atm (%) | 4.9 | 5.7 | 4.9 | 4.7 |
| Distension 12–18 atm (%) | 3.6 | 3.2 | 3.2 | 3.9 |
| Wall Strength (psi) | 30083 | 30079 | 30251 | 30078 |

TABLE 3

Burst and Distension Tests of Pebax 7233 and CBC Chain Extender Compositions

| CBC Conc. (% wt) | 0.25 | 0.25 | 0.25 | 0.25 |
|---|---|---|---|---|
| Extrusion Temperature ° F. | 446 | 410 | 435 | 465 |
| ID × OD (inch) | .0176 × .0342 | .0176 × .0342 | .0176 × .0342 | .0176 × .0342 |
| Balloon size (mm) | 3.0 | 3.0 | 3.0 | 3.0 |
| Double Wall Thickness (inch) | .00143 | .00150 | .00150 | .00150 |
| Burst Pressure (psi) | 362 | 375 | 368 | 368 |
| Distension 6–12 atm (%) | 4.9 | 4.4 | 4.1 | 5.3 |
| Distension 12–18 atm (%) | 3.6 | 4.0 | 3.2 | 3.4 |
| Wall Strength (psi) | 30083 | 29527 | 28976 | 28976 |

Example 2

Brugglen M1251 pellets from Bruggemann Chemical, 50–250 grams (2–5% wt), and 5000 grams of Pebax 7233 pellets from AtoFina were mixed by hand in a plastic bag. The composition was then desiccant dried at 190° F. for 8–12 hours. The mixture was then extruded into tubes, and the tubes formed into balloons as described in Example 1. Table 4 reports the formation and performance data for these balloons.

TABLE 4

Burst and Distension Tests of Pebax 7233 and Brugglen M1251 Chain Extender Compositions

| M1251 Conc. (% wt) | 0 | 2.0 | 5.0 |
|---|---|---|---|
| Extrusion Temperature ° F. | 395 | 465 | 465 |
| ID × OD (inch) | .0215 × .0395 | .0215 × .0395 | .0215 × .0395 |
| Balloon size (mm) | 3.0 | 3.0 | 3.0 |
| Double Wall Thickness (inch) | .00175 | .00159 | .00165 |
| Burst Pressure (psi) | 353 | 346 | 316 |
| Distension 6–12 atm (%) | 6.0 | 5.7 | 5.8 |
| Distension 12–18 atm (%) | 5.7 | 5.4 | 5.1 |
| Wall Strength (psi) | 26700 | 27463 | 23979 |

Example 3

5 Grams (0.1%) of mineral oil from ExxonMobile are added into 5000 grams Pebax 7033 from AtoFina. The two chemicals are mixed by hand in a plastic bag until mineral oil is coated uniformly. 25 Grams(0.5%) of Allinco CBC is then added to the resin mixture and mixed until the CBC powder is even distributed in the resin. The composition is then desiccant dried at 190° F. for 8–12 hours. The mixture is then extruded at a temperature range of 350–475° F. into tubes. The tubes may be blown into balloons, optionally after longitudinal stretching to the tube.

Example 4

Example 3 is repeated except that the polymer is Arnitel EM 740 sold by DSM Engineering Plastics.

Example 5

5 Grams (0.1%) of mineral oil from ExxonMobile are added into 5000 grams Pebax 7233 from AtoFina. The two chemicals are mixed by hand in a plastic bag until mineral oil is coated uniformly. 25 Grams (0.5%) of 1,3-PBO is then added to the resin mixture and mixed until the 1,3-PBO powder is evenly distributed in the resin. The composition is then desiccant dried at 190° F. for 8–12 hours. The mixture is then extruded at a temperature range of 350–475° F. into tubes. The tubes may be blown into balloons, optionally after longitudinal stretching of the tube.

Example 6

Example 3 is repeated except that the polymer is PET, Cleartuf 7207 from Shell Chemical.

Example 7

5 grams (0.1%) of Mineral oil from ExxonMobile is added into 5000 grams polyethylene terephthalate Cleartuf 7207 from Shell Chemical. The two chemicals are mixed by hand in a plastic bag until mineral oil is coated uniformly. 25 Grams (0.5%) of 1,4-PBO is then added into PET resin and mixed until the 1,4-PBO powder is evenly distributed in the resin. The composition is then desiccant dried at 220° F. for 8–12 hours. The mixture is then extruded at temperature range of 370–500° F. into tubes. The tubes may be blown into balloons, suitably after longitudinal stretching of the tube.

Example 8

Example 3 is repeated except that the polymer is PBT, Celanex polybutylene terephthalate from Hoechst Celanese.

Example 9

5 grams (0.1%) of Mineral oil from ExxonMobile was added into 5000 grams Pebax 7233 from AtoFina. The two chemicals were mixed by hand in a plastic bag until the mineral oil was coated uniformly. 12.5 Grams (0.25%) of Allinco CBC was then added into Pebax resin and mixed until the CBC powder was evenly distributed in the resin. The composition was then desiccant dried at 190° F. for 8–12 hours, after which it was extruded into tubes using a multiple zone/multiple heat setting extruder as described in Example 1. The extruder zone temperatures used were: feeding zone 345° F.; barrel zones 365, 395, 446, 446, 446 and 446° F.; and die zone at 403, and 403° F. The balloons were formed and tested as described in Example 1. Table 5 reports the formation and performance data for these balloon which is an average of four balloons.

TABLE 5

Burst and Distension Tests of Pebax 7233 and CBC Chain Extender Compositions

| CBC Conc. (% wt) | 0.25 |
|---|---|
| ID × OD (inch) | .0176 × .0320 |
| Balloon size (mm) | 3.0 |
| Double Wall Thickness(inch) | .00140 |
| Burst Pressure (psi) | 393 |
| Distension 6–12 atm (%) | 5.4 |
| Distension 12–18 atm (%) | 4.2 |
| Wall Strength (psi) | 33176 |

Example 10

In a manner similar to the previous example, tubing samples were prepared from compositions employing Pebax 7233 and varying amounts of CBC chain extender. The extruded tubing was graded for general clarity and observed under a 10× microscope for visible gel particles. Compositions containing 0, and 0.1% CBC produced clear water-white tubes with 0 gel particles. Compositions containing 0.25 0.4 and 0.6% CBC produced slightly opaque tubes with 0 gel particles, an acceptable result. The compositions containing 0.8% CBC produced very opaque tubes with 30 gel particles, an unacceptable result.

The above examples and disclosure are intended to be illustrative and not exhaustive. These examples and the description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A method of preparing a medical device balloon comprising
preparing a polymer composition in melt form, and then extruding the polymer composition to form tubing and blowing a segment of the tubing to form the balloon, without remelting the composition, wherein the step of preparing the polymer composition in melt form comprises
forming a melted reaction mixture comprising
a) at least one terminally reactive polymer and
b) a chain extender and
reacting the reaction mixture.

2. A method as in claim 1 wherein the terminally reactive polymer has at least one terminal active hydrogen and/or carboxylic acid group thereon.

3. A method as in claim 1 wherein the terminally reactive polymer is selected from the group consisting of polyesters; polyamides; polyurethanes; block copolymers incorporating a polyester, polyamide, polyurethane and/or polyether segment.

4. A method as in claim 3 wherein the polymer composition further comprises a polymer selected from the group consisting of polyolefins, poly(meth)acrylate esters, silicones, and organic rubbers.

5. A method as in claim 1 wherein the chain extender comprises a bis-lactam compound.

6. A method as in claim 5 wherein the bis-lactam compound is employed in said reaction mixture in an amount of from about 0.1% to about 5% by weight of the terminally reactive polymer.

7. A method as in claim 5 wherein the bis-lactam compound is a member selected from the group consisting of N,N'-isophthaloyl bis-caprolactam, N,N'-adipoyl bis-caprolactam, N,N'-terephthaloyl bis-laurolactam, N,N'-isophthaloyl bis-butyrolactam, carbonyl bis-caprolactam and mixtures thereof.

8. A method as in claim 1 wherein the chain extender comprises a bis-oxazoline and/or bis-oxazine compound.

9. A method as in claim 8 wherein the bisoxazoline and/or bisoxazine compound is a member selected from the group consisting of 2,2'-bis(2-oxazoline), 2,2-bis(4-methyl-2-oxazoline), 2,2'-bis(4-phenyl-2-oxazoline), 2,2'-bis(4-hexyloxazoline), 2,2'-p-phenylene bis(2-oxazoline), 2,2'-m-phenylene bis(2-oxazoline), 2,2'-tetramethylene bis(4,4'-dimethyl-2-oxazoline) 2,2'-bis(2-oxazine), 2,2-bis(4-methyl-2-oxazine), 2,2'-bis(4-phenyl-2-oxazine), 2,2'-bis(4-hexyloxazine), 2,2'-p-phenylene bis(2-oxazine), 2,2'm-phenylene bis(2-oxazine), 2,2-tetramethylene bis(4,4'-dimethyl-2-oxazine) and mixtures thereof.

10. A method as in claim 8 wherein the bis-oxazoline and/or bis-oxazine compound is employed in said reaction mixture in an amount of from about 0.1% to about 4% by weight of the terminally reactive polymer.

11. A method as in claim 1 wherein the chain extender is incorporated into said reaction mixture in an amount which increases polymer molecular weight but does not substantially promote or induce crosslinking.

12. A method of preparing a medical device comprising
preparing a polymer composition in melt form, and then forming at least a portion of the device from the polymer composition
without remelting the composition, wherein the step of preparing the polymer composition in melt form comprises
forming a melted reaction mixture comprising
a) at least one terminally reactive thermoplastic polymer, and
b) a chain extender and
reacting the reaction mixture.

13. A method as in claim 12 wherein the terminally reactive polymer has at least one active hydrogen and/or carboxylic acid group thereon.

14. A method as in claim 12 wherein said step of forming at least a portion of the device from a thermoplastic polymer composition comprises extruding a tube of said polymer composition.

15. A method as in claim 14 wherein the medical device is a catheter or a balloom.

16. A method as in claim 12 wherein the medical device is a balloon, the method further comprising blowing a segment of the extruded tube at an elevated temperature and pressure to form the balloom.

17. A method as in claim 12 wherein the chain extender is incorporated into said reaction mixture in an amount which increases polymer molecular weight but does not substantially promote or induce crosslinking.

18. A method as in claim 14 wherein said tubing is extruded from an extruder and said reaction mixture is prepared in the extruder.

19. A method claim 1 wherein said tubing is extruded from an extruder and said reaction mixture is prepared in the extruder.

* * * * *